United States Patent
Soskic et al.

(10) Patent No.: US 10,222,388 B2
(45) Date of Patent: Mar. 5, 2019

(54) 25-OH VITAMIN D DERIVATIVES FOR DETERMINING VITAMIN D METABOLITES

(71) Applicant: ORGENTEC DIAGNOSTIKA GMBH, Mainz (DE)

(72) Inventors: Vukic Soskic, Mainz (DE); Robert Poppe, Mainz (DE)

(73) Assignee: ORGENTEC DIAGNOSTIKA GMBH, Mainz (DE)

( * ) Notice: Subject to any disclaimer, the term of this patent is extended or adjusted under 35 U.S.C. 154(b) by 192 days.

(21) Appl. No.: 14/910,881

(22) PCT Filed: Aug. 1, 2014

(86) PCT No.: PCT/EP2014/066620
§ 371 (c)(1),
(2) Date: Feb. 8, 2016

(87) PCT Pub. No.: WO2015/018757
PCT Pub. Date: Feb. 12, 2015

(65) Prior Publication Data
US 2016/0195556 A1 Jul. 7, 2016
US 2017/0115313 A9 Apr. 27, 2017

(30) Foreign Application Priority Data
Aug. 7, 2013 (DE) .................. 10 2013 215 580

(51) Int. Cl.
C07D 495/04 (2006.01)
C07C 401/00 (2006.01)
G01N 33/82 (2006.01)

(52) U.S. Cl.
CPC ........... *G01N 33/82* (2013.01); *C07C 401/00* (2013.01); *C07D 495/04* (2013.01); *C07C 2601/14* (2017.05); *C07C 2602/24* (2017.05)

(58) Field of Classification Search
CPC ............ C07C 2601/14; C07C 2602/24; C07C 401/00; C07D 495/04; G01N 33/82
See application file for complete search history.

(56) References Cited

U.S. PATENT DOCUMENTS

| | | |
|---|---|---|
| 4,119,647 A | 10/1978 | Liebman et al. |
| 5,116,573 A | 5/1992 | Yamada |
| 5,478,816 A | 12/1995 | Shah |
| 5,981,779 A | 11/1999 | Holick et al. |
| 6,017,908 A | 1/2000 | Reddy |
| 6,291,693 B1 | 9/2001 | Holick et al. |
| 6,455,714 B1 | 9/2002 | Holick et al. |
| 6,787,660 B1 | 9/2004 | Armbruster |
| 8,003,400 B2 | 8/2011 | Kobold |
| 2002/0107411 A1 | 8/2002 | Holick et al. |
| 2008/0317764 A1 | 12/2008 | Huber |
| 2010/0075435 A1 | 3/2010 | Kasagi |
| 2016/0047825 A1 | 2/2016 | Poppe |

FOREIGN PATENT DOCUMENTS

| | | |
|---|---|---|
| CH | 681891 A5 | 6/1993 |
| CN | 101467048 A | 6/2009 |
| CN | 102628872 A | 8/2012 |
| DE | 102013205055 A1 | 9/2014 |
| EP | 0603726 A2 | 6/1994 |
| EP | 2030026 B1 | 12/2009 |
| GB | 2285805 A | 7/1995 |
| JP | 2002506429 A | 2/2002 |
| JP | 2010053118 A | 3/2010 |
| WO | 9724127 A1 | 7/1997 |
| WO | 2007079394 A2 | 7/2007 |

OTHER PUBLICATIONS

Okamura et al., "Studies on vitamin D (calciferol) and its analogs. 13. 3-Deoxy-3α-methyl-1α-hydroxyvitamin D3, 3-deoxy-3α-methyl-1α,25-dihydroxyvitamin D3, and 1α-hydroxy-3-epivitamin D3. Analogs with conformationally biased a rings," J. Org. Chem., 1978, 43 (4), pp. 574-580.*

Sheves et al., "Conformational analysis of flexible trans-dienes by polarization spectroscopy," Israel J. Chem., 1979, vol. 18, pp. 359-363.*

Kósa et al., "Preparation and Spectral Characterization of Fluorescence Probes Based on 4-N,N-Dimethylamino Benzoic Acid and Sterically Hindered Amines," J. Fluoresc., 2012, vol. 22, No. 5, pp. 1371-1381.*

Kamao et al., "C-3 Epimerization of Vitamin D3 Metabolites and Further Metabolism of C-3 Epimers," J. Biol. Chem., 2004, vol. 279, No. 16, pp. 15897-15907.*

Singh et al., "C-3 Epimers Can Account for a Significant Proportion of Total Circulating 25-Hydroxyvitamin D in Infants, Complicating Accurate Measurement and Interpretation of Vitamin D Status," J. Clin. Endocrinol. Metab., 2006, vol. 91, issue 8, pp. 3055-3061.*

Achmatowicz et al., "The first synthesis and biological testing of the enantiomer of 1α,25-dihydroxyvitamin D3," Tetrahedron Lett., 2001, vol. 42, issue 15, pp. 2891-2895.*

A printout retrieved from http://www.organic-chemistry.org/namedreactions/mitsunobu-reaction.shtm on Feb. 22, 2018.*

A printout retrieved from http://www.organic-chemistry.org/namedreactions/gabriel-synthesis.shtm on Feb. 22, 2018.*

(Continued)

*Primary Examiner* — Galina Yakovleva
(74) *Attorney, Agent, or Firm* — Millen White Zelano & Branigan (57) ABSTRACT

The present invention relates to new vitamin D compounds which are bonded to a labelling group at the C3 stereocentre by means of a linker. The present invention further relates to a method for producing these vitamin D compounds and to the use of an intermediate for producing these compounds. The present invention also relates to a method for quantitatively determining vitamin D using a vitamin D compound according to the invention as a tracer. Furthermore, the present invention relates to a reagent for determining vitamin D, containing a compound according to the invention, and to the use thereof for determining vitamin D.

3 Claims, 5 Drawing Sheets

(56) References Cited

OTHER PUBLICATIONS

Higashi et al., "Characterization of new conjugated metabolites in bile of rats administered 24,25 dihydroxyvitamin D3 and 25-hydroxyvitamin D3", Steroids, 2000, vol. 65, pp. 281-294.

Wasner et al., "Synthesis and characterization of monomeric cordycepinlipid conjugates model substances for biodegradable ester and carbonate linkages in conjugates and potential inhibitors of HIV-1-replication", Helvetica Chimica Acta, 1996, vol. 79, p. 609-618.

Patil et al., "Synthesis, characterization and in vitro evaluation of novel vitamin D3 nanoparticles as a versatile platform for drug delivery in cancer therapy", Journal of Materials Chemistry B, 2013, 1, pp. 5742-5750.

Wasner et al., "Synthesis and characterization of cordycepin-trimervitamin and -lipid conjugates potential inhibitors of HIV-1-replication", Helvetica Chimica Acta, 1996, vol. 79, pp. 619-633.

Kobayashi et al., "Specificity of polyclonal antibodies raised against a novel 24,25-dihydroxyvitamin D3-bovine serum albumin conjugant linked through the C-11alpha or C-3 position", J. Steroid Biochem. Molec. Biol., 1997, vol. 62, No. 1, pp. 79-87.

Kobayashi et al., "Production and specificity of antisera raised against 25-hydroxyvitamin D3-(C-3)-bovine serum albumin conjugates", Steroids, 1992, vol. 57(10), pp. 488-493.

Roy and Ray, "Aminopropylation of vitamin D hormone (1 alpha,25-dihydroxyvitamin D3), its biological precursors, and other steroidal alcohols: an anchoring moiety for affinity studies of sterols" Steroids, 1995, 60(8): 530-533.

International Search Report for PCT/EP2014/066620 dated Sep. 5, 2014.

Parvaz et al., "Production of monoclonal antibodies to dehydroepiandrosteronesulphate after immunization of mouse with dehydroepiandrosterone-bovine serum albumin conjugate", J. steroid Biochem., 1989, vol. 32, No. 4, pp. 553-558.

Machine translaton of DE69713138 T2 issued Jan. 16, 2003 to Laurie David/ Immundiagnostic Systems Ltd.

Higashi et al., "Enzyme-linked immunosorbent assay for plasma 24, 25-dihydroxyvitamin D3", Analytica Chimica Acta, 1998, 365, pp. 151-158 (previously cited).

* cited by examiner

Fig. 1

Continuation of Fig. 1

25-OH VITAMIN D DERIVATIVES FOR DETERMINING VITAMIN D METABOLITES

The present invention relates to new vitamin D compounds which are bonded to a labelling group at the C3 stereocentre by means of a linker. The present invention further relates to a method for producing these vitamin D compounds and to the use of an intermediate for producing these compounds.

The present invention also relates to a method for quantitatively determining vitamin D using a vitamin D compound according to the invention as a tracer. Furthermore, the present invention relates to a reagent for determining vitamin D, containing a compound according to the invention, and to the use thereof for determining vitamin D.

For humans, adequate provision with vitamin D is essential. The most frequent physiological forms of vitamin D are vitamin $D_3$ or vitamin $D_2$. The most important physiologically active derivatives of vitamin $D_3$ (cholecalciferol) are 25OHD3 (25-hydroxy vitamin $D_3$ or calcidiol) and 1,25-(OH)$_2$ $D_3$ (1-alpha, 25-dihydroxy vitamin $D_3$ or calcitriol). Generally, most vitamin $D_3$ is not absorbed with food like other vitamins but is produced in the skin under the influence of UV light. Here, 7-dehydrocholesterol is converted by UV irradiation into provitamin $D_3$, the unstable intermediate being reorganised into vitamin $D_3$. In food, vitamin $D_3$ is contained especially in oily fish. A further form of vitamin D which can occur in the body is vitamin $D_2$ (calciferol or ergocalciferol), which occurs in fungi and can be absorbed with food. Vitamin $D_3$ and vitamin $D_2$ preparations represent a further source for provision with a sufficient amount of vitamin D.

Vitamin D and its natural derivatives are extremely hydrophobic molecules. In the blood, vitamin D is transported in a complex with vitamin D-binding protein (DBP). DBP belongs to the family of the albumins and binds vitamin D, vitamin D metabolites and fatty acids.

In the liver, vitamin D is oxidised by cytochrome P450 at position C-25. The resulting 25OHD (25-hydroxy vitamin $D_3$ or 25-hydroxy vitamin $D_2$) is the vitamin D metabolite mainly present in the circulation. The concentration of 25OHD in serum serves as an indicator for evaluating the vitamin D status of humans.

In the kidneys and in other tissues, 25OHD is converted to 1,25(OH)$_2$D, the physiologically active form of vitamin D, which, after binding to the vitamin D receptor (VDR), controls vitamin D-dependent regulated (VDRE) gene activities.

Adequate provision with vitamin D is important for normal bone structure and for regulating calcium and phosphate resorption. Activation of VDR with 1,25(OH)$_2$D increases the efficiency of intestinal calcium uptake by about 30% and phosphate uptake by about 80%. If the serum concentration of 25OHD falls below 30 ng/ml, this is associated with a significant reduction in calcium resorption in the intestine and an increase in parathyroid hormone concentration. Vitamin D deficiency is an important factor for osteoporosis with an increased risk of bone fracture and is associated with further health risks. While the concentration of vitamin D in serum is subject to considerable variations depending on food intake and exposure to the sun, the 25OHD serum concentration is a good indicator for determining the vitamin D provision status. The 25OHD concentration in serum is therefore routinely determined in medical diagnostics.

25OHD in serum is preferably determined by competitive binding analysis. Here, the 25OHD concentration of the sample is determined by displacing a radioactively or chemically labelled vitamin D derivative from a vitamin D binding protein, e.g. a 25OHD-specific antibody. The labelled vitamin D derivative used in the competitive binding assay as a tracer has to bind to the vitamin D binding protein used in the assay with a high affinity and specificity.

DE 69713138 (Immundiagnostic Systems Ltd.) describes 1,25 dihydroxy vitamin D derivatives that are radioactively modified at the C20 position and can be used as tracers in immunoassays.

U.S. Pat. No. 5,116,573 (Kureha Kagaku Kogyo Kabushiki Kaisha) describes vitamin D derivatives that are deuterium-labelled or tritium-labelled at the C19 and C6 position.

Alternatively, the 3β hydroxy group of vitamin D3 and vitamin derivatives may be used for introducing non-radioactive labelling groups, the hydroxy groups being modified to form an ester bridge or ether bridge. The ability to use vitamin D tracers based on hapten-labelled ester derivatives is, however, severely limited for example by the instability of the ester bridges at pH values above pH 7 and the susceptibility thereof to esterases, which are often present in biological fluids and tissues. In order to solve this problem, methods for converting the hydroxy group into a 3β aminopropyl ether derivative have been developed (Roy, A. and Ray, R., *Steroids*. 1995, 60: 530-533, U.S. Pat. No. 6,291,693: Holick, M. F. and Ray, U.S. Pat. No. 6,787,660: Armbruster, M. P. et al., US20080317764: Huber, E. et al., U.S. Pat. No. 8,003,400: Kobold, U.).

These prior-art methods for producing vitamin D derivatives and the use thereof as tracers in a competitive binding assay involve a range of drawbacks, however. Radioactively labelled vitamin D tracers have a shorter storage life and a reduced stability. In addition to the inherent drawbacks for health and the environment, the costs of storage, transport and disposal increase for radioactive reagents.

The vitamin D derivatives that are modified at the 3β hydroxy group have the drawback that the synthetic route is extremely labour-intensive, and highly flammable and aggressive reagents have to be used under strictly anaerobic conditions. In addition, the compounds sometimes only have low stability under physiological conditions, and this severely limits the use thereof in samples of biological origin.

A tracer that is used to determine vitamin D should be synthetically easily available, should not contain any labelling groups for detection that are potentially harmful to health and should be suitable for use in automatable test methods.

The object of the present invention is therefore to provide a labelled vitamin D compound which solves the previous problems in the synthesis of labelled vitamin D derivatives and is suitable for use as a tracer in an automated method for quantitatively determining vitamin D.

The limitations and drawbacks of the labelled vitamin D compounds described in the prior art and of the production thereof are overcome at least in part by the present invention.

The present invention provides labelled vitamin D compounds which are suitable as tracers in test methods for determining vitamin D and are synthetically available by means of simple and brief access.

Surprisingly, it has been found that a labelling group can be inserted into the vitamin D parent substance by nucleophilic substitution of the hydroxy group at the C3 atom. Here, the configuration at the C3 atom is inverted. Nevertheless, the resulting compounds having a labelling group in a configuration at the C3 atom are surprisingly extremely suitable as a tracer in competitive vitamin D determining methods. The inverse conformational structure at C3 is primarily advantageous due to an associated increase in the stability in biological fluids such as blood, for example against esterases.

By means of the present invention, new tracers and a reliable and automatable method for determining the concentration of vitamin D, in particular of 25-hydroxy vitamin $D_3$ or 25-hydroxy vitamin $D_2$, are provided.

A first aspect of the present invention therefore relates to a vitamin D compound having a structure according to formula (I), wherein
R is a $C_2$-$C_{10}$ alkyl or alkenyl group, which is optionally substituted by a hydroxy group,
L is a linker, and
W is a labelling group that is not a vitamin D compound.

The expression "$C_2$-$C_{10}$ alkyl" refers to linear or branched alkyl groups having 2 to 10 carbon atoms. This expression covers groups such as ethyl, n-propyl, iso-propyl, n-butyl, iso-butyl, tert-butyl, n-pentyl, n-hexyl, n-heptyl, n-octyl, 2-ethylhexyl, 2-octyl, 3-octyl, iso-octyl, n-nonyl, 2-nonyl, 3-nonyl, 4-nonyl, iso-nonyl, n-decyl, iso-decyl, 2-decyl and 3-decyl. Each hydrogen atom can also be replaced by a deuterium atom.

The expression "$C_2$-$C_{10}$ alkenyl" refers to alkenyl groups having 2 to 10 carbon atoms. These may be straight-chained or branched, and may be in the Z or E form. Such groups contain vinyl, propenyl, 1-butenyl, iso-butenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g. 1,3- or 2,4-pentadienyl, (E)-5,6 dimethylhept-3-enyl and (Z)-5,6 dimethylhept-3-enyl. Each hydrogen atom can also be replaced by a deuterium atom.

The expression "labelling group" refers to a group which can be detected by physical, chemical and/or biochemical methods, is compatible with the use of the labelled molecule and is in particular not radioactive. In this case, this is not a vitamin D compound having a structure according to formula (I).

The expression "linker" refers to a molecular spacer which bonds a vitamin D basic structure according to formula (I) to a labelling group.

In one embodiment, the linker is characterised in that it has a chain length of from 6 to 110 atoms, selected from C atoms and optionally heteroatoms such as N, O and/or S. The chain length is preferably 8-80, 12-60 or 30-50 atoms. The heteroatoms optionally contained in the linker are preferably N and/or O.

In one embodiment, the linker is represented by the formula (II):

wherein
Q2 is: —C(O)NR$^1$—., —C(O)O—., —C(S)NR$^1$—., —C(S)O—., —C(O)S—., —C(S)S—., —O—., —S—., —NR$^1$—., —CH$_2$O—., —CH$_2$S—. or —CH$_2$NR$^1$—.,
Q1 is: —C(O)—., —NR$^2$C(O)—., —NR$^2$C(S)—., —OC(O)—., —C(O)NR$^2$—., —C(S)NR$^2$—., —C(S)—., —OC(S)—., —SC(O)—., —SC(S)—., —O—., —S—. or —NR$^2$—.,
Y is: —O— or —CH$_2$—,
R1 and R2, independently of each other, are H or $C_1$-$C_6$ alkyl, and
m is 1-30, and
n is 1-12,
Q1 being bonded to the group W and Q2 being bonded to the parent substance of the vitamin D compound according to formula (I), and in each case (.) representing the binding site of Q2 to the parent substance of the vitamin D compound or of Q1 to the group W. Each hydrogen atom can also be replaced by a deuterium atom.

The expression "$C_1$-$C_6$ alkyl" refers to linear or branched alkyl groups, which comprise 1 to 6 carbon atoms, in particular 1-3 carbon atoms. These groups contain methyl, ethyl, n-propyl, iso-propyl, n-butyl, iso-butyl, tert-butyl, n-pentyl, neopentyl, 1-ethylpropyl, n-hexyl and iso-hexyl. Each hydrogen atom can also be replaced by a deuterium atom.

Preferred embodiments are characterised in that
Q2 is: —C(O)NR$^1$—., —C(O)O—., —C(S)NR$^1$—., —C(S)O—., —C(O)S—., —C(S)S—.,
Q1 is: —C(O)—., —NR$^2$C(O)—., —NR$^2$C(S)—., —OC(O)—., —C(O)NR$^2$—., —C(S)NR$^2$—., —C(S)—., —OC(S)—., —SC(O)—., —SC(S)—., —O—., —S—. or —NR$^2$—.,
Y is: —O— or —CH$_2$—,
R$^1$ and R$^2$, independently of each other, are H or $C_1$-$C_6$ alkyl, and
m is 1-30, and
n is 1-12,
or
Q2 is: —C(O)NR$^1$—., —O—., —S—., —NR$^1$—., —CH$_2$O—., —CH$_2$S—. or —CH$_2$NR$^1$—.,
Q1 is: —C(O)—., —NR$^2$C(O)—., —NR$^2$C(S)—., —OC(O)—., —C(O)NR$^2$—., —C(S)NR$^2$—., —C(S)—., —OC(S)—., —SC(O)—., —SC(S)—., —O—., —S—. or —NR$^2$—.,
Y is: —O— or —CH$_2$—,
R$^1$ and R$^2$, independently of each other, are H or $C_1$-$C_6$ alkyl, and
m is 1-30, and
n is 1-12.

Another preferred embodiment is characterised in that
Q2 is: —C(O)NR$^1$—.,
Q1 is: —C(O)—., —NR$^2$C(O)—., —OC(O)—., —C(O)NR$^2$—., —O—., —S—. or —NR$^2$—.,
Y is: —O—,
R$^1$ and R$^2$, independently of each other, are H or $C_1$-$C_6$ alkyl and in particular H,
m is 1-30, and
n is 1-12.

The group Y in a linker according to formula (II) is preferably —O—.

In another preferred embodiment, the vitamin D compound has a structure according to formula (Ia), wherein
R is a $C_2$-$C_{10}$ alkyl or alkenyl group, which is optionally substituted by a hydroxy group,
m is 1-30, and
W is a labelling group that is not a vitamin D compound.

In yet another preferred embodiment, the vitamin D compound has a structure according to formula (Ib)

The labelling group W may either be a group which is directly detectable or a group which is indirectly detectable, for example after binding to a complementary, detectable binding partner.

Directly detectable groups are, for example, dyes, enzymes, electrochemically detectable groups or luminescent groups such as fluorescent groups, phosphorescent groups or chemiluminescent groups, which for example can be detected using optical methods.

An electrochemically detectable group is understood to be a group which can undergo an electron transfer reaction with a reaction partner, electrons being transferred from one reaction partner to the other. The detectable group is either reduced and the reaction partner is oxidised, or the detectable group is oxidised and the reaction partner is reduced.

A fluorescent group is understood to be a fluorescent dye which, after excitation, spontaneously emits light that is lower in energy than the previously absorbed light. Preferably, the fluorescent group is a dye such as fluorescein, rhodamine, stilbene, fluorescent proteins such as green fluorescent protein (GFP), yellow fluorescent protein (YFP) and red fluorescent protein (RFP), coumarin, quinine, allophycocyanin, synthetic fluorescence labels or tracers such as or according to formula (Ic)

ATTO dyes (ATTO-TEC GmbH, Siegen), Alexa Fluor (Molecular Probes, Invitrogen Corp., Carlsbad) and cyanine such as Cy3, Cy5 and Cy7 and derivatives thereof.

A phosphorescent group is understood to be a chemical group which, after excitation, emits light over a relatively long time period, resulting in phosphorescence of split seconds to hours.

A chemiluminescent group is a chemical group which emits electromagnetic radiation in the visible-light range or infrared range by means of a chemical reaction. Chemiluminescent tracers include luminol, acridinium esters and polyhistidine tracers.

Indirectly detectable groups are, for example, biotin, which can be detectable by labelled avidin or strepavidin, antigens and haptens, which can be detected by labelled, specific antibodies, carbohydrate structures, which can be detected by lectins, or affinity tags.

The expression biotinyl also includes derivatives of biotinyl, provided that these bind to streptavidin or avidin.

In a preferred embodiment, W is biotinyl, a fluorescent group or a chemiluminescent group.

In another preferred embodiment, W is biotinyl.

The group R is preferably a vitamin D side chain, in particular having an OH group, such as a structure according to formula (III):

(III)

or a structure according to formula (IV)

(IV)

Particularly preferably, R has a structure according to formula (III).

A second aspect includes a method for producing a vitamin D compound having a structure according to formula (I), comprising the steps of:

(a) nucleophilically substituting, at the hydroxy group of the C3 atom, a compound having a structure according to formula (V):

(V)

wherein R is a $C_2$-$C_{10}$ alkyl or alkenyl group, which is optionally substituted by a hydroxy group, wherein the hydroxy group is replaced by a group X with inversion of the configuration at the C3 stereocentre, in order to obtain a compound having a structure according to formula (VI), (VI)

wherein R is a $C_2$-$C_{10}$ alkyl or alkenyl group, which is optionally substituted by a hydroxy group, and X is an optionally protected hydroxy group, thiol group or primary or secondary amino group, and (b) coupling a labelling group W which is not a vitamin D compound to the group X of the compound having a structure according to formula (VI) via a linker, in order to obtain a compound having a structure according to formula (I).

The nucleophilic substitution carried out in step (a) preferably includes reacting the alcohol (V) with an alkyl phosphine, for example tri-n-butylphosphine, or an aryl phosphine, for example triphenylphosphine or diphenyl(2-pyridyl) phosphine, an alkyl azodicarboxylate such as diethyl azodicarboxylate or diisopropyl azodicarboxylate and a nucleophilic group X, preferably a slightly acidic nucleophilic group, in a suitable solvent such as tetrahydrofuran or diethyl ether.

The nucleophilic group X may be introduced in protected or free form. Preferably, the group X is introduced in protected form.

A "protected" form means that this is a precursor group which for example, depending on functionality, comprises suitable protective groups, which are well known to a person skilled in the art, it being possible to convert this protected form into the corresponding unprotected group by means of methods that are known in the prior art.

The compound for introducing the group X is preferably selected from the group comprising imides, amines, hydrazoic acid, carboxylic acids, alcohols, thiols, thiocarboxylic acids or salts thereof. The compound is preferably an imide, amine or hydrazoic acid, more preferably an imide or hydrazoic acid and most preferably a phthalimide or salts thereof. These groups can, where necessary, be deprotected into a corresponding hydroxy group, thiol group or primary or secondary amino group by means of appropriate methods which are known to a person skilled in the art. For example, phthalimide can be converted into the corresponding primary amine by primary amines such as methylamine or hydrazine in a suitable solvent.

The group R is preferably a vitamin D side chain, preferably having an OH group, such as a structure according to formula (III) or according to formula (IV).

The coupling in step (b) of a labelling group W as defined above to the group X in a compound having a structure according to formula (VI) via a linker as defined above is carried out in accordance with methods that are known to a person skilled in the art. Preferably, a linker which is already bound to a labelling group W is coupled to the group X. Preferably, in this case the linker comprises a group that is reactive with X, for example a leaving group such as N-hydroxysuccinimidyl, which can be substituted with the group X, as a result of which the group X is bound to the linker in order to produce a compound having a structure according to formula (I).

A third aspect of the present invention relates to an in-vitro method for quantitatively determining vitamin D in a sample using a compound having a structure according to formula (I) as a tracer.

The expression "tracer" refers to a compound which comprises a group which is directly detectable or indirectly detectable, for example after binding to a complementary detectable binding partner. Preferably, the detection is carried out using chemical, physical or biochemical methods, preferably using physical and biochemical methods such as spectroscopic methods or immunological assays.

Unless otherwise indicated, the expression "vitamin D" includes all naturally occurring compounds which have the vitamin D2 basic structure or the vitamin D3 basic structure or the vitamin D3 basic structure according to the structural formulae (VII) or (VIII).

Formula (VII)

Formula (VIII)

The numbering of the carbon atoms in the structural formulae (VII) and (VIII) is in accordance with steroid nomenclature. 25-Hydroxy vitamin D denotes vitamin D metabolites which are hydroxylated at position 25 of the structural formulae (VII) or (VIII), that is to say 25-hydroxy vitamin $D_2$ and 25-hydroxy vitamin $D_3$. Further hydroxy vitamin D compounds are, for example, 1,25-dihydroxy vitamin D or 24,25-dihydroxy vitamin D.

1,25-Dihydroxy vitamin D refers to the active forms of vitamin D (the D hormones), which are hydroxylated at position 1 as well as at position 25 of the structural formulae (VII) and (VIII).

Other well-known vitamin D compounds are 24,25-dihydroxy vitamin D2, 24,25-dihydroxy vitamin D3 and C3-epi-25-hydroxy vitamin D.

In one embodiment, the in-vitro method comprises the steps of:
(a) contacting a vitamin D-containing sample with the tracer,
(b) quantitatively determining the tracer under conditions in which the detected quantity of tracer allows a conclusion to be drawn as to the overall concentration of vitamin D in the sample.

The vitamin D in step (a) may be present in free form. In another embodiment, the vitamin D is present in bound form, and step (a) further comprises releasing the bound vitamin D.

The expression "releasing bound vitamin D" means the complete or partial separation of vitamin D from complexes with proteins, in particular DBP, to which it may be bound in biological samples. Preferably, substantially all of the vitamin D present in the sample is released. In this connection, "substantially" means that at least 90%, 95%, 98% and preferably at least 99% of the vitamin D is released.

Suitable release agents are known to a person skilled in the art and include organic substances such as pamoic acid or 8-anilino-1-naphthalenesulfonic acid (8-ANS), inorganic substances such as alkali bases in combination with reducing agents or biochemical substances such as the serine proteinase proteinase K.

A release reagent which comprises at least one hydrotropic substance such as toluenesulfonic acid, at least one transition metal salt such as an iron(III) salt, for example iron(III) chloride or iron(III) citrate, and optionally a complexing agent such as citrate, EDTA and/or a salt thereof, as described in DE 10 2013 205 055.0, is particularly suitable.

The determination of vitamin D according to step (b) can be carried out after step (a) or together with step (a).

Preferably, step (b) is carried out at the same time as step (a), and as a result a one-step method for determining vitamin D in a sample is provided.

The overall concentration of vitamin D is determined in step (b) preferably by determining the tracer in an immunological method in which the tracer is bound to an immunological partner in order to form an immune complex. The expression "immunological binding partner" includes antibodies.

A competitive immunological method is particularly preferably used for determining the concentration of vitamin D in step (b).

Suitable competitive test formats are well known to a person skilled in the art. In a typical competitive binding assay, a receptor or antibody having a tracer, that is to say a labelled form of vitamin D, is contacted with the sample to be tested. The amount of tracer which is found bound to the receptor or antibody is indicative of the proportion of unlabelled vitamin D in the sample. Alternatively, a competitive binding assay can include contacting a receptor or antibody bound to a tracer with the sample to be tested and measuring the amount of displaced tracer, which is indicative of the amount of vitamin D in the sample. The tracer comprises a labelling group as defined above, which is in particular selected from biotinyl, a fluorescent group or a chemiluminescent group, which are as defined above.

In the most preferred embodiment, a tracer labelled with biotin is used and detection is carried out by means of peroxidase-labelled streptavidin.

In particular, an antibody is used in step (b) for determining the tracer, which antibody specifically recognises the side chain R of a compound having a structure according to formula (I) and specifically recognises a vitamin D3 or vitamin D2 side chain which has a hydroxy group at the C25 atom.

The tracer is preferably added to the sample in a quantity to set a final concentration of from 0.2-100 ng/ml, in particular of from 5-50 ng/ml, of the tracer.

The sample to be tested is preferably a biological fluid selected, for example, from blood, serum, plasma or milk. The sample is usually from a living being, preferably from a mammal, for example from a human.

The vitamin D to be determined by the method according to the invention comprises a hydroxy group at the C25 atom and includes, for example, 25-hydroxy vitamin D3, 25-hydroxy vitamin D2, 1,25-dihydroxy vitamin D3, 1,25-dihydroxy vitamin D2 and mixtures thereof. The vitamin D compounds are particularly preferably 25-hydroxy vitamin D3 and/or 25-hydroxy vitamin D2.

A fourth aspect of the present invention relates to a reagent for determining vitamin D, comprising a compound according to formula (I).

Preferably, the reagent further comprises a reagent for releasing bound vitamin D and optionally diluting agents, carriers, solvents, adjuvants, stabilisers, preservatives and/or dispersants.

The reagent is preferably present as a dry or wet reagent.

A fifth aspect of the present invention is the use of the above-described reagent for determining vitamin D, in particular in the in-vitro method according to the invention as described above.

A sixth aspect of the present invention is the use of a compound having a structure according to formula (VI):

(VI)

wherein R is a $C_2$-$C_{10}$ alkyl or alkenyl group, which is optionally substituted by a hydroxy group,
X is $NHR^3$, OH or SH, and
$R^3$ is H or $C_1$-$C_6$ alkyl,
for producing a tracer compound, that is to say a compound having a structure according to formula (I), formula (Ia), formula (Ib) or formula (Ic), in particular for producing a compound having a structure according to formula (I), formula (Ib) or formula (Ic).

Each hydrogen atom can also be replaced by a deuterium atom.

The group R is preferably a vitamin D side chain, preferably having an OH group, such as a structure according to formula (III) or according to formula (IV).

The present invention will be described in greater detail below by means of the following drawings and examples.
Legend to the Figures.

BRIEF DECRIPTION OF FIGURES

EXAMPLE 1

Figure 1:
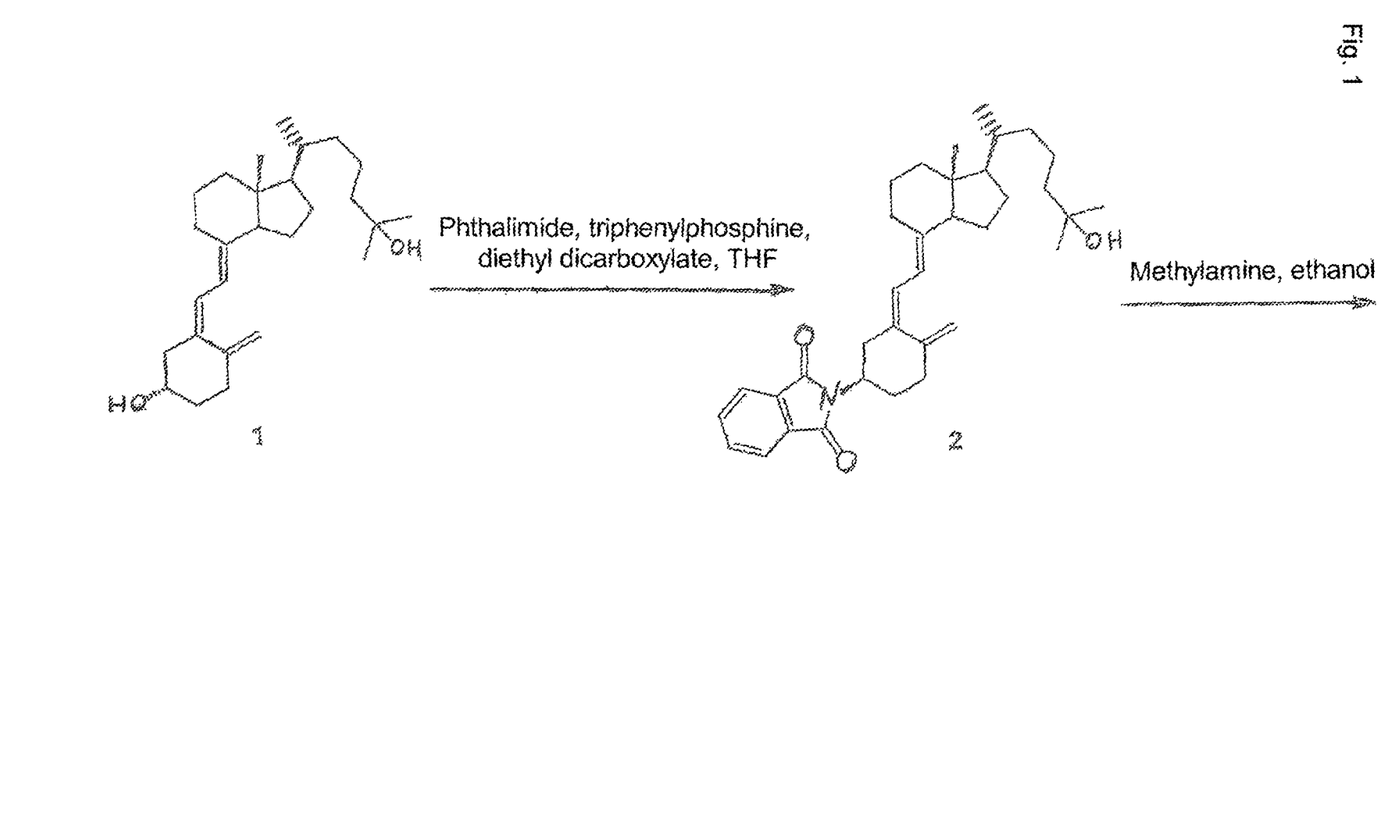
FIG. 1: Synthesis of a biotin 25-OH vitamin D3 tracer reagent by converting 25-hydroxy vitamin D3 (1) into the epimer 3α N-phthalimido derivative (2), deprotecting to form the amino derivative (3) and reacting with NHS-PEG$_{12}$ biotin to form 3α-[α-biotinamide-ω-dodeca(ethylene glycol)-amide]-25-hydroxy-deoxyvitamin D3 (4).

Synthesis of 3α-[α-biotinamide-ω-dodeca(ethylene glycol)-amide]-25-hydroxy-deoxyvitamin D3 (FIG. 1)

$^1$H-NMR (at 300 MHz) spectra were recorded on a Bruker AC300 (Bruker, Karlsruhe, Bruker) using the solvent $CDCl_3$. The evaluation was carried out in ppm with tetramethylsilanes as the internal standard. The mass spectra were determined on a Varian MAT 311 spectrometer (70 eV, EI). F.256 silica gel plates (Merck Darmstadt, Germany) were used for the analytical thin-layer chromatography. Chromatographic purification was carried out in silica gel columns, 230-400 mesh ASTM. All the reagents were obtained from Sigma Aldrich.

1.1: Synthesis of 3α-phthalimide-25-hydroxy-deoxyvitamin D3

A solution of 25-hydroxy-vitamin D3 (10.0 mg, 25 µmol), phthalimide (4.5 mg, 31.25 µmol), triphenylphosphine (8.2 mg, 31.25 µmol) and diethylazodicarboxylate (5.4 mg, 31.25 µmol) in tetrahydrofuran (2.0 ml) was stirred at room temperature for 24 hours. After hexane (2.0 ml) was added, the mixture was filtered through a silica gel filter. After the solvent was removed, the solids were resuspended in 5 ml 10% $Na_2CO_3$ and were extracted twice using 10 ml diethyl ether each time. The combined ether phases were dried over $MgSO_4$ and concentrated under vacuum to form a colourless oil. The product was purified by silica gel column chromatography. 3α-phthalimide-25-hydroxy-deoxyvitamin D3 (FIG. 1, formula 2) was isolated in the form of a colourless oil (7.3 mg). NMR: δ 0.58 (s, H—C(18), 3H), 0.85 (d, J=6.4 Hz, H—C(21), 3H), 1.21 (s, H—C(26 and 27), 6H), AB quartet: 4.84 (d, J=2.4 Hz, H—C(19)E, 1H) and 5.06 (d, J=1.9 Hz, H—C(19)Z, 1H), AB quartet: 6.02 (d, J=11.0 Hz, H—C(7), 1H) and 6.26 d, J=11.0 Hz, H—C(6), 1H), 7.80 (m, Ar, 4H), MS: m/e (100) 529.24 (M$^+$).

1.2: Synthesis of 3α-amino-25-hydroxy-deoxyvitamin D3

3α-Phthalimide-25-hydroxy-deoxyvitamin D3 (2), (7.2 mg, 13.5 mmol) was dissolved in 0.5 ml 8M methylamine in ethanol in a nitrogen atmosphere. The mixture was first stirred for 2 hours at room temperature and then for 16 hours at 4° C. The solvent was evaporated at negative pressure and the residue was resuspended in 5 ml 10% $Na_2CO_3$ and was extracted three times using 10 ml diethyl ether each time. The combined ether phases were dried over $MgSO_4$ and concentrated under vacuum to form a colourless oil. The product was purified by silica gel column chromatography. 3α-Amino-25-hydroxy-deoxyvitamin D3 was isolated as a colourless oil (4), (5.2 mg). NMR: δ 0.57 (s, H—C(18), 3H), 0.85 (d, J=6.4 Hz, H—C(21), 3H), 1.21 (s, H—C(26 and 27), 6H), AB quartet: 4.83 (d, J=2.4 Hz, H—C(19)E, 1H) and 5.00 (d, J=1.8 Hz, H—C(19)Z, 1H), AB quartet: 5.97 (d, J=11.0 Hz, H—C(7), 1H) and 6.27 d, J=11.0 Hz, H—C(6), 1H), MS: m/e (100) 400.37 (M$^+$).

1.3: Synthesis of 3α-[α-biotinamide-ω-dodeca(ethylene glycol)-amide]-25-hydroxy-deoxyvitamin D3

3α-Amino-25-hydroxy-deoxyvitamin D3 (3), (5.2 mg, 12.9 µmol) triethylamine (0.02 µL), NHS-$PEG_{12}$-biotin (9.4 mg, 10.0 µmol, Thermo Scientific, Prod. No. 21312) were dissolved in 0.2 ml dimethylformamide and stirred at room temperature overnight. The solvent was evaporated at negative pressure and the residue was purified by silica gel column chromatography. Here, 5.9 mg 3α-[α-biotinamide-w-dodeca(ethylene glycol)-amide]-25-hydroxy-deoxyvitamin D3 (4) was obtained in the form of a colourless wax. NMR: δ 0.58 (s, H—C(18), 3H), 0.85 (d, J=6.4 Hz, H—C(21), 3H), 1.21 (s, H—C(26 and 27), 6H), 3.62 (m, H—C(ethylene glycol), 50H), AB quartet: 4.84 (d, J=2.4 Hz, H—C(19)E, 1H) and 5.06 (d, J=1.9 Hz, H—C(19)Z, 1H), AB quartet: 6.02 (d, J=11.0 Hz, H—C(7), 1H) and 6.26 (d, J=11.0 Hz, H—C(6), 1H), MS: m/e (100) 1247.80 (M+Na$^+$).

EXAMPLE 2

Preparation of a Vitamin D Release Reagent

Sodium toluenesulfonate was dissolved in water and adjusted with stock solutions of 1 M sodium citrate and 1 M iron(III) chloride to a final concentration of 1 M sodium toluenesulfonate, 100 mM sodium citrate and 50 mM iron (III) chloride.

EXAMPLE 3

Binding of a 25-OHD Antibody to a Solid Phase

An antibody against 25-OH-vitamin D3 or 25-OH-vitamin D2 was diluted in Tris-buffered saline pH 8.0 to a concentration of 1 µg/ml. The wells of a microtitre plate (Maxisorb, Nunc) were coated with 100 µl of the diluted antibody, dried at 37° C. and stored at 4° C. until the test was carried out.

EXAMPLE 4

Competitive Binding Analysis

Figure 2:
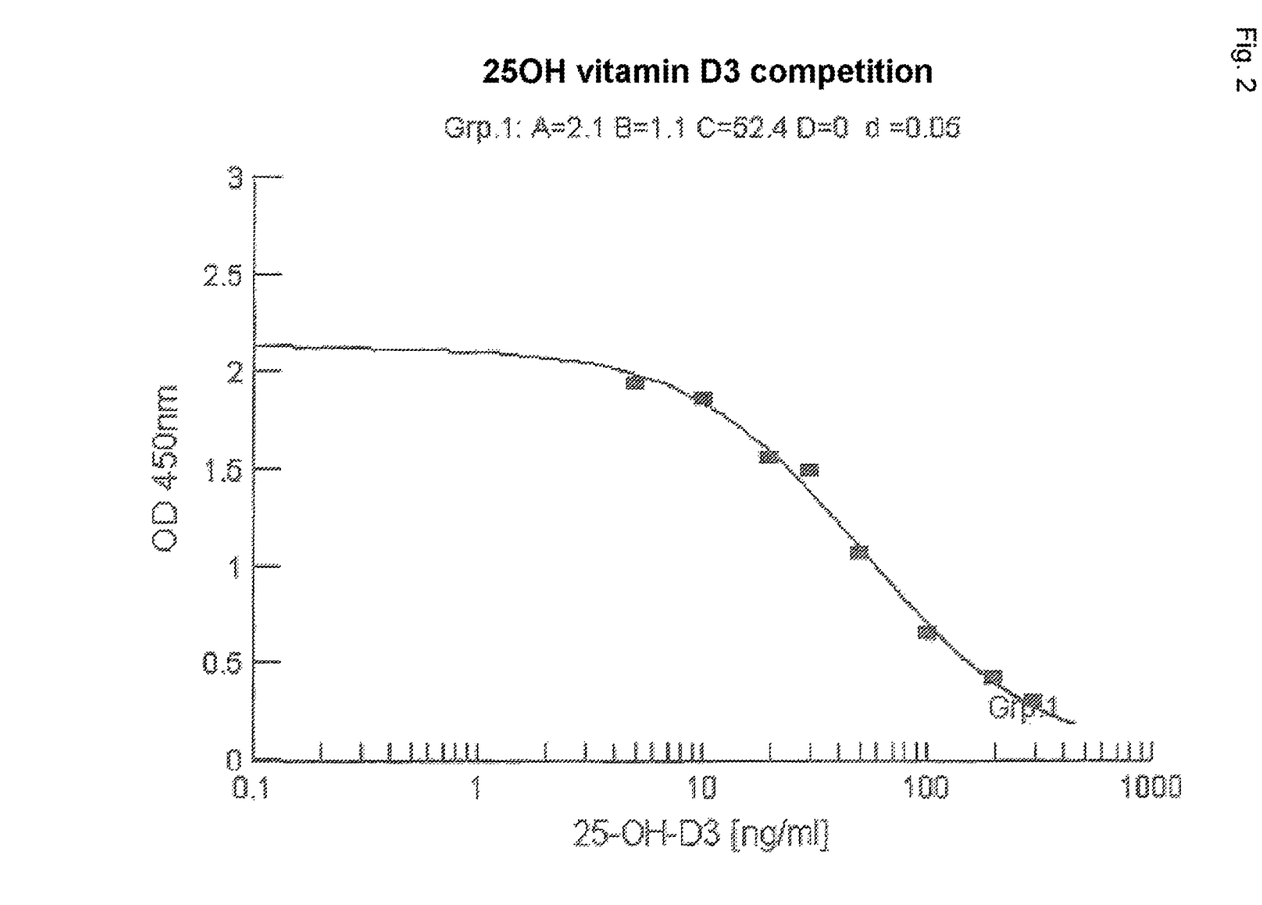
FIG. 2: Characterisation of the competitive displacement of defined 25OHD3 concentrations by a biotin-25OHD3 tracer reagent. For the ELISA detection of the specific 25OHD competition, 80 µl of vitamin D release reagent were added to serial dilutions of 25OHD3 in vitamin D-free serum matrix (SerCon, Seracare Inc.) in concentrations of 0, 5, 10, 20, 20, 50, 100, 200, 300 ng/ml in the presence of 7.5 ng/ml of biotin-25OHD tracer reagent and applied to microtitre plate wells coated with an anti-25OHD antibody. The binding of the tracer on the basis of the competing 25OHD concentration was determined with peroxidase-labelled streptavidin and a tetramethylbenzidine (TMB) colour reaction by measuring the OD 450 nm.

Defined concentrations of 25-OHD3 were added to vitamin D-free serum matrix (Seracon, Seracare Inc.). In each case 80 µl of the concentration series were introduced into a microtitre plate well pre-loaded with 3α-[α-biotinamide-ω-dodeca(ethylene glycol)-amide]-25-hydroxy-deoxyvitamin D3 (25OHD-biotin tracer reagent) from example 1 as a tracer and incubated for 5 minutes at RT (20-27° C.) for resolubilisation of the tracer reagent. 80 µl of the release reagent from example 2, which dissociates vitamin D in the sample from the complex with DBP, were then added to the sample batch and mixed. 100 µl of the samples diluted with vitamin D release reagent were transferred into wells coated with 25OHD antibody and incubated for 30 minutes at RT. The 25OHD contained in the sample now competes with the 25OHD biotin tracer for binding sites on the 25OHD antibody. The sample batch was then removed and the wells were rinsed three times with 200 µl of wash buffer each time. The antibody-bound biotin-25OHD tracer was detected with peroxidase-labelled streptavidin and a tetramethylbenzidine (TMB) colour reaction. After the substrate reaction had been stopped by addition of 100 µl of 50 mM phosphoric acid, the optical density was measured at 450 nm. Here, a specific competition of the biotin-25OHD tracer was demonstrated, as shown in FIG. 2, even at a 25OHD3 concentration of 5 ng/ml.

EXAMPLE 5

Determination of 25-Hydroxy Vitamin D in Serum or Plasma in the Automated Alegria™ 25-OH Vitamin D3/D2 Test System In order to study the correlation between HPLC+LC-MS/MS-based 25OHD3/D2 determination methods and the automated Alegria™ 25-OH vitamin D3/D2 test system (ORG270, Orgentec Diagnostika GmbH), serum or plasma samples, the 25OHD3/D2 concentration of which was characterised by HPLC+LC-MS/MS-based methods (6PLUS1 Multilevel Serum Calibrator Set 25-OH-Vitamin D3/D2, Chromsystems GmbH), and dilutions thereof were stored in aliquots at −20° C. until the determination.

For the determination, in each case 80 µl of the samples were placed in well A of the Alegria™ test strip. The 8 wells of a test strip contained the vitamin D release reagent from example 2, streptavidin-HRP conjugate, TMB substrate, a 25OHD calibrator solution and 25-OHD antibody-coated wells for in each case one sample determination. Test processing took place automatically in the Alegria™ machine. Inside a test strip, the sample and the calibrator, internal to the test strip, were in each case mixed with 25OHD-biotin tracer and vitamin D release reagent, transferred to the 25OHD antibody-coated wells and washed after being incubated for 30 minutes. The antibody-bound biotin-25OHD tracer was detected with peroxidase-labelled streptavidin and a tetramethylbenzidine (TMB) colour reaction by measuring the optical density at 650 nm.

Figure 3:
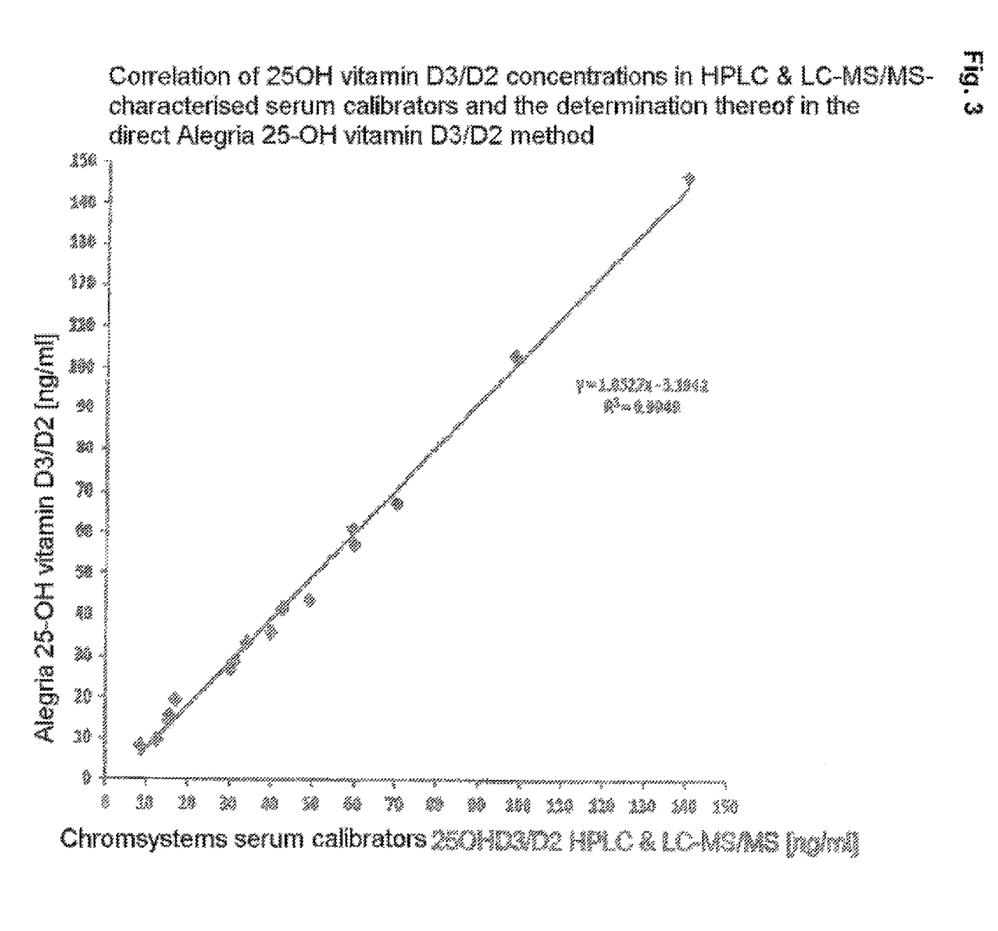
FIG. 3: The comparative analysis of serums with defined 25OHD3 and 25OHD2 concentrations (6PLUS1 Multilevel Serum Calibrator Set 25-OH-Vitamin D3/D2, Chromsystems GmbH) and dilutions thereof in vitamin D-free serum matrix (SerCon, Seracare Inc.) showed a high correspondence between the HPLC- and LC-MS/MS- defined 25-OHD3/D2 concentrations and the direct 25-OH vitamin D3/D2 determination method using the automatic Aleria™ system (ORG270, ORGENTEC).

As is shown in FIG. 3, a high correspondence was observed between the HPLC and LC-MS/MS-defined 25-OHD3/D2 concentrations in serum samples and the direct 25-OH vitamin D3/D2 determination method in the automated Alegria™ system.

EXAMPLE 6

Determination of the Serum Stability of 25-OH Vitamin D Derivatives

For comparative testing of the serum stability of biotin 25-OH vitamin D derivatives, the test compounds were incorporated in a vitamin D-free serum matrix (Seracon, Seracare Inc.). In a first batch (VD1), the 25-OH vitamin D derivative 3α-[α-biotinamido-ω-dodeca(ethylene glycol)-amido]-25-hydroxy-deoxyvitamin $D_3$ that is in accordance with example 1 and is present at the C3 atom in the non-natural (R) configuration was set to a concentration of 3 ng/ml in a vitamin D-free serum matrix. In a second batch (VD2), the 25-OH vitamin D derivative 3β-3'[α-biotinamido-ω-dodeca(ethylene glycol)-amido]amidopropyl-ether-25-hydroxy-vitamin $D_3$ that is in accordance with US20080317764 and is present at the C3 atom in the natural (S) configuration was set to a concentration of 3 ng/ml in a vitamin D-free serum matrix.

Aliquots of 1 ml each of the batches VD1 and VD2 were stored at −20° C. and were incubated for 24 hours at 37° C. The samples were then equilibrated for 1 hour at room temperature (22° C.). 500 µl of each of the reference samples stored at −20° C. and of each of the samples incubated for 24 hours at 37° C. were added to and mixed with 500 µl release reagent according to example 2 in each case. 100 µl of the samples diluted with vitamin D release reagent were transferred into 25OHD antibody-coated wells according to example 3 and were incubated at room temperature for 30 minutes, so that the biotin-25-OH vitamin D derivatives present in the samples bound to the 25OHD antibody.

The sample batches were then removed and the wells were rinsed three times with 200 µl of wash buffer each time. The antibody-bound biotin-25-OH vitamin D derivatives were detected with peroxidase-labelled streptavidin and a tetramethylbenzidine (TMB) colour reaction. After the substrate reaction had been stopped by addition of 100 µl of 50 mM phosphoric acid, the optical density was measured at 450 nm.

Figure 4:
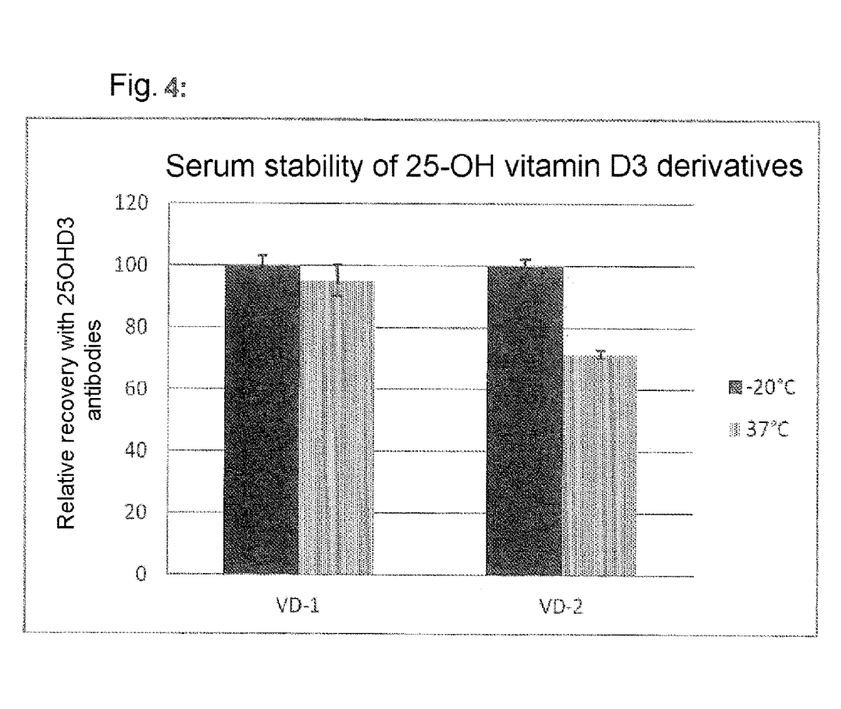
FIG. 4: The comparative determination of the recovery of dilutions of the 25-OH vitamin D derivatives 3α-[α-biotinamido-ω-dodeca(ethylene glycol)-amido]-25-hydroxy-deoxyvitamin $D_3$ (VD1) and 3β-3'[α-biotinamido-ω-dodeca (ethylene glycol)-amido]amidopropyl-ether-25-hydroxy vitamin $D_3$ (VD2) in vitamin D-free serum matrix after 24-hour incubation at 37° C. exhibits a high serum stability of the derivative VD1 present at the C3 atom in the (R) configuration compared with the VD2 present at the C3 atom in the (S) configuration.

This demonstrated, as shown in FIG. 4, a recovery of 95.2% for the 3α-[α-biotinamido-ω-dodeca(ethylene glycol)-amido]-25-hydroxy-deoxyvitamin $D_3$ derivative in batch VD1 after incubation for 24 hours at 37° C., compared with the reference sample stored at −20° C. The 3β-3'[α-biotinamido-ω-dodeca(ethylene glycol)-amido]amidopropyl-ether-25-hydroxy vitamin $D_3$ derivative present in batch VD2 has a significantly lower serum stability. In this case, a recovery of only 71.5% was detected after incubation for 24 hours at 37° C., compared with the reference sample stored at −20° C.

The invention claimed is:
1. A compound having a structure according to formula (Ib)

(Ib)

or formula (Ic)

(Ic)

2. A compound according to claim 1, having a structure according to formula (Ib)

(Ib)

3. A compound according to claim 1, having a structure according to formula (Ic)

(Ic)

* * * * *